United States Patent [19]

Allaire et al.

[11] Patent Number: 5,341,812
[45] Date of Patent: Aug. 30, 1994

[54] ELECTROCARDIOGRAPH MONITOR SYSTEM AND ADAPTOR

[75] Inventors: Michael J. Allaire; Jeffrey W. Stone, both of Cincinnati, Ohio

[73] Assignee: NDM Acquisition Corp., Minneapolis, Minn.

[21] Appl. No.: 56,714

[22] Filed: May 3, 1993

[51] Int. Cl.⁵ ............................................. A61N 5/04
[52] U.S. Cl. ................................................... 128/696
[58] Field of Search ..................... 128/639, 696, 710

[56] References Cited

U.S. PATENT DOCUMENTS

| | | | |
|---|---|---|---|
| 3,629,789 | 12/1971 | Szeremy | 339/033 |
| 4,121,575 | 10/1978 | Mills et al. | 128/639 |
| 4,215,236 | 7/1980 | Reiser | 128/696 |
| 4,280,507 | 7/1981 | Rosenberg | 128/696 |
| 4,353,372 | 10/1982 | Ayer | 128/696 |
| 4,494,552 | 1/1985 | Heath | 128/696 |
| 4,550,735 | 11/1985 | Akamatsu et al. | 128/696 |
| 4,632,121 | 12/1986 | Johnson et al. | 128/639 |
| 4,640,563 | 2/1987 | LeBlanc | 128/639 |
| 4,740,167 | 4/1988 | Millhimes et al. | 439/092 |
| 4,746,298 | 5/1988 | Hollander | 439/222 |
| 4,806,112 | 2/1989 | Roberts et al. | 439/144 |
| 5,007,863 | 4/1991 | Xuan | 439/639 |
| 5,046,965 | 9/1991 | Neese et al. | 439/372 |
| 5,052,725 | 10/1991 | Meyer et al. | 289/308 |

OTHER PUBLICATIONS

New Dimensions In Medicine, "Cable Leadwire & Accessory Catalog/1991-1992," 1991, p. 2.

Primary Examiner—William E. Kamm
Attorney, Agent, or Firm—Killworth, Gottman, Hagan & Schaeff

[57] ABSTRACT

An electrocardiograph system is provided wherein a single electrocardiograph cable may be used to interconnect a plurality of lead wires extending from a plurality of associated medical electrodes with a number of different ECG monitors. Each ECG monitor is connected to an adaptor which properly interconnects each monitor with the single electrocardiograph cable. A wire locking mechanism may be provided at one end of the electrocardiograph cable for securely coupling the lead wires to the cable. Further, a cable coupling mechanism may be provided at the other end of the cable for securely coupling the cable to the adaptor.

6 Claims, 5 Drawing Sheets

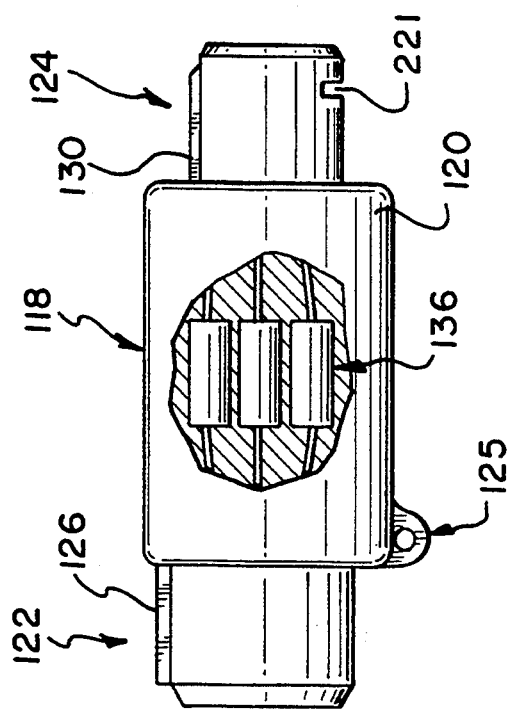
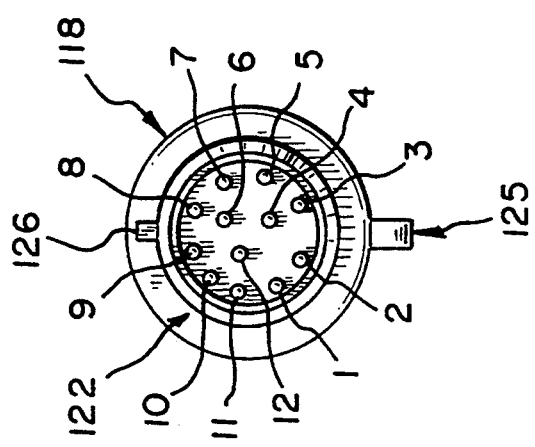

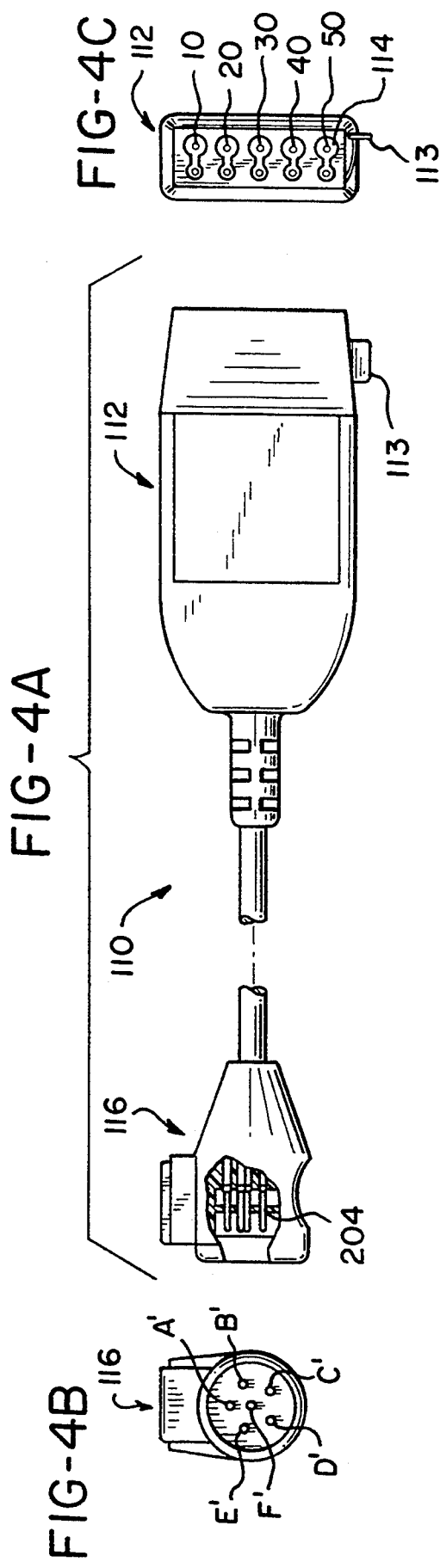

ELECTROCARDIOGRAPH MONITOR SYSTEM AND ADAPTOR

BACKGROUND OF THE INVENTION

The present invention generally relates to an electrocardiograph apparatus, and more particularly, to an adaptor arrangement for electrically connecting each of a plurality of electrocardiograph apparatuses to a plurality of medical electrodes via a common electrocardiograph cable.

Modern technological advances in medicine have required hospitals and other medical facilities to purchase and maintain increasingly complex and expensive diagnostic equipment. A required diagnostic instrument in any modern medical facility is an electrocardiograph (also referred to herein as ECG) apparatus or monitor which assists a physician in detecting heart disease and heart defects by monitoring physiological electric potentials indicative of muscular activity of the heart. The electrocardiograph apparatus monitors heart muscle activity via a plurality of medical electrodes applied to the body of a patient. Typically, the electrodes are connected to lead wires which, in turn, are connected to one end of a single ECG cable. The ECG cable has a connector on its opposite end which can be plugged into a particular ECG monitor.

Most medical facilities have a plurality of electrocardiograph monitors stationed throughout their treatment, and recovery areas. It is common for a set of electrodes to be applied to a patient, and left in place for an extended period of time. It is also common for a patient to be moved a number of times within the facility. Consequently, the same set of electrodes affixed to a patient are sequentially connected to a series of ECG monitors as the patient is transferred from area to area. For example, a patient may be connected to a stationary ECG monitor while confined to a hospital bed. During transit of the patient, a mobile ECG monitor may be employed. A further ECG monitor may be used at the patient's destination. Accordingly, technicians must be able to connect the patient electrodes quickly to a number of ECG monitors as the patient moves throughout the facility.

At the present time, there are over 2,000 different ECG monitors on the market. Each of these monitors requires an ECG cable of a specific mechanical and electrical design to interconnect the monitor with the lead wires. As can be appreciated, ECG cables are frequently misplaced or lost. This problem is accentuated since many hospitals and medical centers employ different ECG monitors from floor to floor and even within the same room. Consequently, valuable time and resources are expended locating the correct ECG cable when connecting a patient to a particular ECG monitor. In addition, hospitals must spend an excessive amount of time and money storing, inventorying and reordering the numerous ECG cables required at their facilities.

Other problems may arise when an electrically incompatible ECG wire cable is capable of being mechanically connected to a particular ECG monitor. Although the ECG monitor may appear to be functioning correctly, the data being produced may be erroneous due to the faulty electrical connection between the ECG monitor and the medical electrodes.

It is thus apparent that a need exists for an adaptor arrangement for an ECG monitor which substantially limits the number of different ECG cables needed for use with a wide variety of ECG monitors, yet ensures proper operation of the monitors.

SUMMARY OF THE INVENTION

This need is met by an electrocardiograph system in accordance with the present invention wherein a series of adapters are connected to different ECG monitors to permit proper connection of the different ECG monitors to a plurality of medical electrodes through a common electrocardiograph cable. Thus, the heretofore experienced problems associated with requiring different electrocardiograph cables for connection to different ECG monitors are eliminated.

In accordance with one aspect of the present invention, an adaptor is provided for an electrocardiograph apparatus or monitor which includes an input connector having one of a plurality of input connector configurations. The electrocardiograph apparatus conventionally monitors activity of the heart muscle of a patient via electrical signals detected by medical electrodes attached to the patient. The electrical signals are transmitted from the electrodes to the electrocardiograph apparatus by an electrocardiograph cable which includes a cable connector connected at one end thereof.

The adaptor includes a machine coupling means, which may include at least one male circular male element, for electrically interconnecting with the electrocardiograph apparatus via the input connector. A circuit means is provided in the adaptor for conditioning the electrical signals so that the electrical signals may be properly received by the electrocardiograph apparatus. Finally, a cable coupling means electrically interconnects the cable connector and the circuit means whereby the electrocardiograph apparatus properly receives the electrical signals detected by the medical electrodes and monitors the heart muscle of the patient.

Preferably, the adaptor further comprises attachment means, such as a lanyard, for mechanically securing the adaptor to the electrocardiograph apparatus. Additionally, the cable coupling means may include at least one plunger contact positioned so as to electrically connect with the cable connector.

In another aspect of the present invention, an electrocardiograph system is provided for connecting an electrocardiograph apparatus to a plurality of lead wires extending from a plurality of medical electrodes. The system includes an electrocardiograph cable for transmitting electrical signals detected by the medical electrodes.

A first end of the cable is connected to the plurality of lead wires and a second end of the cable, opposite the first end, includes a cable connector for connection to an adaptor. The cable connector preferably includes a cable locking mechanism for securely coupling the cable connector to the adaptor. The first end may include an electrode block for connection to both shielded and unshielded lead wires. The electrode block preferably has a wire locking mechanism which secures the lead wires thereto.

The adaptor, capable of being coupled to the cable connector of the cable and to the input connector of the electrocardiograph apparatus, transmits the electrical signals from the cable to the electrocardiograph apparatus and conditions the electrical signals so that the electrical signals may be properly received by the electrocardiograph apparatus.

Preferably, the cable connector includes at least one electrical contact post and the adaptor includes at least one plunger contact for electrically connecting with the at least one electrical contact post and for providing a zero extraction force during separation of the cable connector and the adaptor.

In yet another aspect of the present invention, an electrocardiograph cable for electrically connecting to a plurality of medical electrodes, having an associated plurality of lead wires, that detect electrical signals representative of heart muscle activity of a patient to an electrocardiograph apparatus is provided. The electrocardiograph apparatus includes an input connector having one of a plurality of input connector configurations. The input connector has an adaptor attached thereto.

An electrode block at a first end of the cable electrically interconnects the electrocardiograph cable and the plurality of lead wires. A cable connector electrically couples the electrocardiograph cable and the adaptor at a second end of the cable opposite the first end whereby the electrocardiograph apparatus properly receives the electrical signals generated by the plurality of medical electrodes.

In a further aspect of the present invention, a hospital electrocardiograph patient monitoring system including a plurality of electrocardiograph monitors is provided. The monitors having various ones of a plurality of input connector configurations. A plurality of adapters are connected to an associated one of the plurality of monitors. Each of the adapters has an appropriate machine coupling means for connection to the associated input connector, and an identical cable coupling means.

In yet another aspect of the present invention, an adaptor for interconnecting an electrocardiograph monitor having one of a plurality of input connectors, and an electrocardiograph cable is provided. The adaptor includes a housing having machine coupling means mounted on a first end for connecting with the one of the plurality of input connectors and a cable coupling means mounted on a second end for connecting with the electrocardiograph.

It is thus an object of the present invention to provide an improved electrocardiograph system for transmitting electrical signals indicative of a patient's heart activity from a plurality of medical electrodes to a number of different ECG monitors. An adaptor is connected to each ECG monitor which properly connects to a common electrocardiograph cable. Thus, the electrocardiograph cable may be used with numerous ECG apparatuses and, consequently, eliminating the problems associated with having different electrocardiograph cables for different ECG apparatuses.

Other objects and advantages of the invention will be apparent from the following description, the accompanying drawings and the appended claims.

BRIEF DESCRIPTION OF THE DRAWINGS

FIG. 3A shows the end of the adaptor which connects to the ECG monitor;

FIG. 3B is a partially broken away, side view of the adaptor;

FIG. 3C shows the end of the adaptor which connects to the cable connector;

FIG. 4A shows the electrocardiograph cable wherein the cable connector is cutaway to show the internal male circular elements;

FIGS. 4B and 4C are end views of the cable connector and electrode block, respectively, of the electrocardiograph cable; and Table 4 is a tabulation of the connections between the male circular elements of the cable connector and the female receptacles of the electrode block.

DETAILED DESCRIPTION OF THE INVENTION

Figure 1:
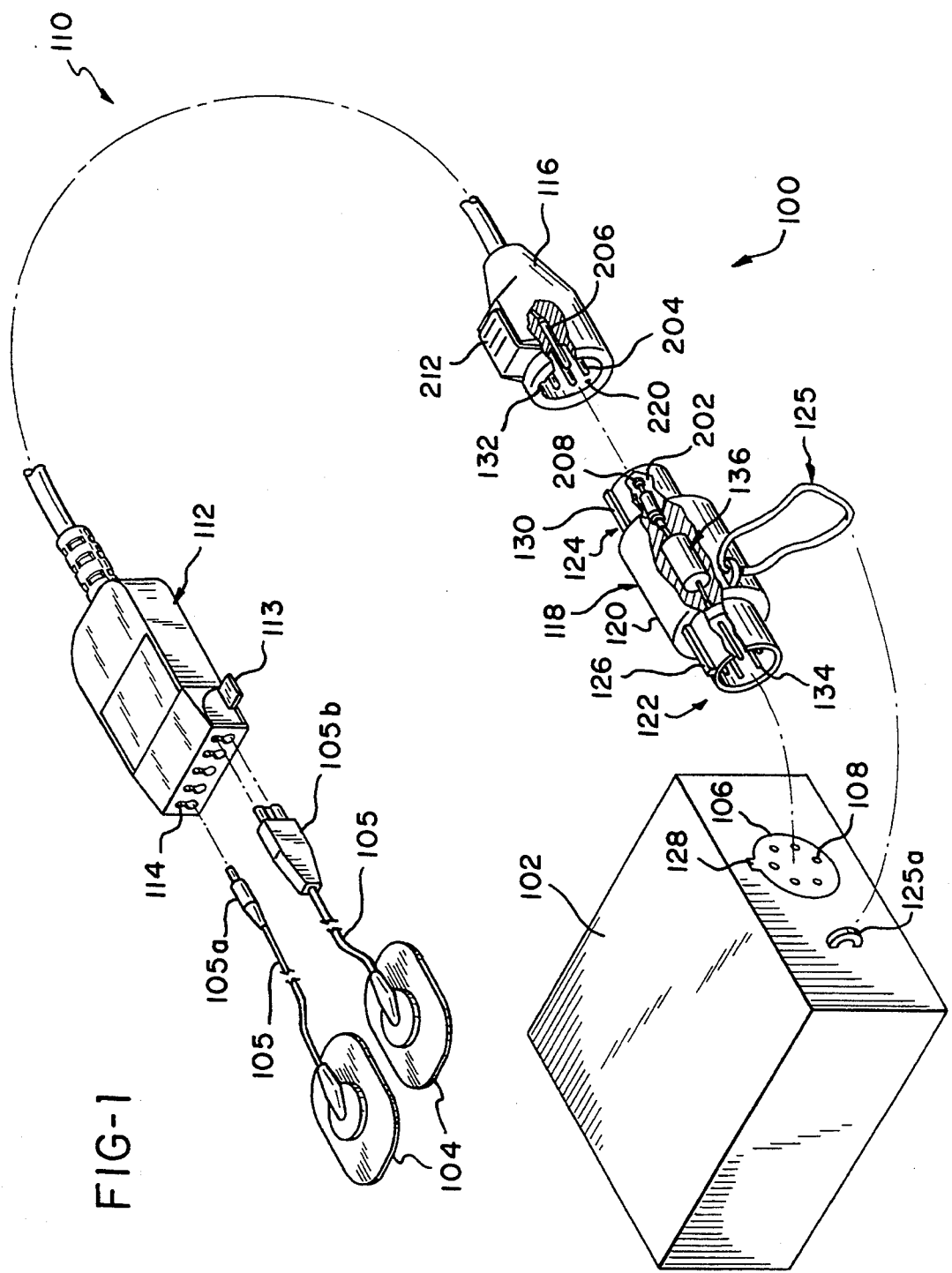
FIG. 1 shows an electrocardiograph system including an electrocardiograph cable and adaptor for connecting a plurality of medical electrodes to an ECG monitor in accordance with the present invention.

An electrocardiograph system 100 for connecting an electrocardiograph apparatus or monitor 102 to a plurality of medical electrodes 104 in accordance with the invention is shown in FIG. 1. Each of the medical electrodes 104 is connected to an associated one of a plurality of lead wires 105 via a plurality of connectors 105a and 105b which transmit electrical signals generated by the electrode 104. The electrocardiograph (ECG) apparatus or monitor 102 monitors physiological heart potentials of a patient via electrical signals produced by medical electrodes 104 and generates a trace. The trace may be displayed, recorded, analyzed or otherwise evaluated by apparatus 102, providing a diagnostic tool for detecting heart disease or defects. The ECG apparatus 102 includes an input connector 106 which is in one of a plurality of possible configurations. Although the input connector 106 is shown having six female receptacles 108, other connector configurations may be used advantageously with the invention. Typically, conventional ECG monitors will include an input connector having between two and fifteen female or male connectors.

The plurality of lead wires 105 are connected to an electrocardiograph or ECG cable 110 via an electrode block 112 at one end of the ECG cable 110. A conventional wire locking mechanism, shown as a movable lever 113, may be provided for securely attaching the lead wires 105 to the electrode block 112. Although the electrode block 112 is shown having five female receptacles 114 for attaching either shielded lead wires 105A or unshielded lead wires 105B, the electrode block 112 may be easily designed to accept any number of shielded and unshielded lead wires. Typically, the female receptacles 114 internally contain one or more male pins for connecting to the lead wires.

At the opposite end of the ECG cable 110 is a cable connector 116 which can be removably attached to an adaptor 118. Cable connector 116 includes contact posts, or pins 204, each of which is electrically connected to an associated one of the receptacles 114 by a separate electrical conductor extending through ECG cable 110. The adaptor 118 comprises a housing 120 having a machine coupling means 122 mounted in a first end for connecting with the input connector 106 and a cable coupling means 124 mounted in a second end for connecting with the cable connector 116 of the ECG cable 110. An attachment means, such as a lanyard 125, locking ring or any other conventional mechanism, may be provided on the housing 120 to securely fasten the adaptor 118 to the ECG apparatus 102 in a well-known manner, such as by securing the lanyard 125 through an opening 125a in the ECG apparatus 102. A raised guide 126 may be provided on the first end of the housing 120 for mating with a corresponding keyway 128 in the input connector 106 in a well-known manner to assure that the adaptor 118 and the input connector 106 are properly aligned during coupling. Similarly, a raised guide 130 on the second end of the housing 120 mates with a corresponding keyway 132 in the cable connector 116 to assure that the adaptor 118 and the cable connector 116 are properly aligned.

The machine coupling means 122 will vary in configuration depending on the make and model of the monitor 102 with which it is designed to be used. The machine coupling means 122 of the adaptor 118 in the example shown in the drawings includes a plurality of male circular elements 134. Each male circular element 134 has a corresponding female receptacle 108 in the input connector 106 such that electrical connections are completed therebetween upon coupling of the adaptor 118 and the input connector 106. Alternatively, the male circular elements may be located on the input connector with corresponding female receptacles on the machine coupling means. It should be understood that the number, shape and placement of the male circular elements 134 will depend upon the number, shape and placement of the female receptacles 108 of the particular ECG monitor 102.

A circuit means comprising a plurality of electrical components, such as resistor 136, electrically interconnects the machine coupling means 122 and the cable coupling means 124 of the adaptor 118. The circuit means 136 conditions the electrical signals received from the cable coupling means 124 so that the signals may be properly received by the ECG monitor 102.

Figure 2A:
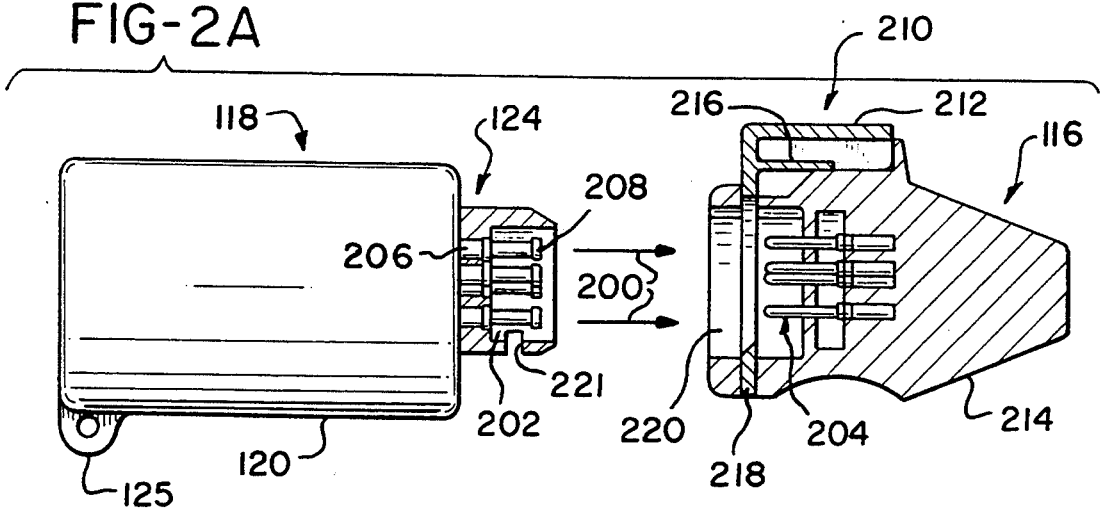
FIGS. 2A through 2C are partial cutaway views of the adaptor and cable connector of the electrocardiograph cable of FIG. 1.

The connection between the cable connector 116 of the ECG cable 110 and the cable coupling means 124 of the adaptor 118 will now be described with reference to FIGS. 2A through 2C. FIG. 2A shows the cable connector 116 and the cable coupling means 124 in the uncoupled position. Arrows 200 indicate the relative movement of the respective elements 116 and 118 during coupling. Adaptor 118 has a plurality of plunger contacts 202 which abut corresponding electrical contact pins 204 in the cable connector 116 when the adaptor 118 and cable connector 116 are coupled. The plunger 202 is comprised of a cylindrical base 206 and a center shaft 208 slidably mounted within the base 206. A biasing means, such as a spring mounted within the base 206, provides a force which resists further insertion of the center shaft 208 into the base 206.

Consequently, the biasing means forces the center shaft 208 against the corresponding contact pin 204 to assure contact therebetween when the adaptor 118 and cable connector 116 are coupled. Furthermore, the force generated by the biasing means assists in uncoupling the adaptor 116 and cable connector 118, thus providing a zero extraction force on the adaptor 116. Alternatively, the plunger contacts 202 may be positioned on the cable connector 116 and the contact pins 204 positioned on the adaptor 118.

The cable connector 116 includes a cable locking mechanism, shown as push button assembly 210, for securely coupling the adaptor 118 to the cable connector 116. A push button 212 actuates the coupling and uncoupling of the adaptor 118 and the cable connector 116. In the uncoupled position, shown in FIG. 2A, the push button 212 is maintained above the body 214 of the cable connector 116 by a resilient member 216. The push button assembly 210 also includes a blade 218 movably connected to the push button 212 whereby a downward movement of the push button 212 causes concomitant downward movement of the blade 218. When uncoupled, the blade 218 extends into the interior of an adaptor orifice 220 into which the cable coupling means 124 of the adaptor 118 is to be inserted. When coupled, the blade 218 is disposed in a corresponding notch 221 formed in the cable coupling means 124, thus prohibiting uncoupling without removing the blade 218 from the notch 221.

Figure 2B:
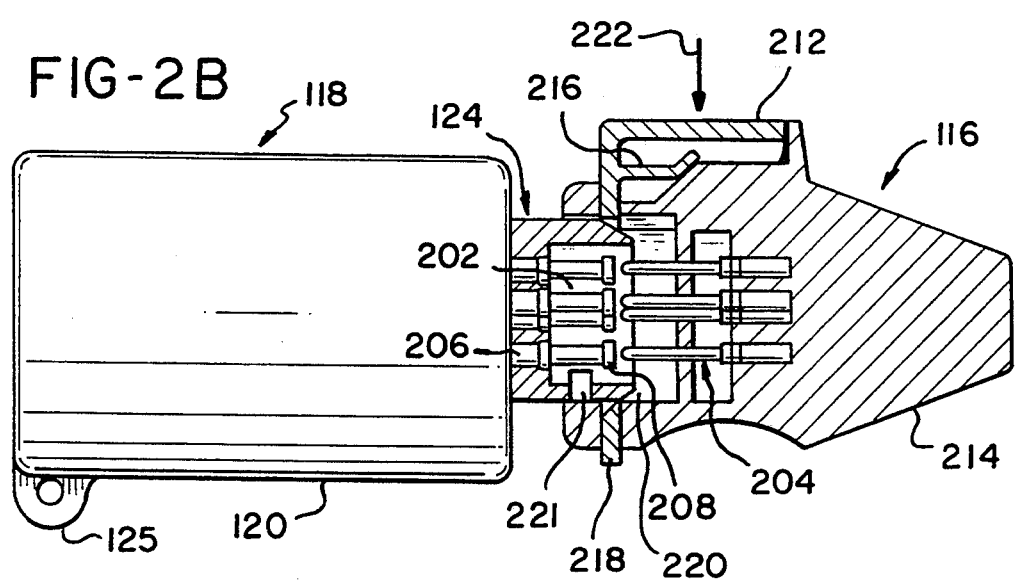

FIG. 2B shows the cable coupling means 124 of the adaptor 118 partially inserted into the adaptor orifice 220 of the cable connector 116. A force, indicated by arrows 222, applied to the push button 212 bends the resilient member 216 and withdraws the blade 218 from the interior of the adaptor orifice 220 to permit insertion of the cable coupling means 124. The plurality of plunger contacts 202 are now aligned with their respective contact pins 204. As noted above, a raised guide 130 may be formed on the housing 120 of the cable connector means 124 for entering a corresponding keyway formed in the adaptor orifice 220 to assure proper alignment of the plunger contacts 202 and contact pins 204.

Figure 2C:
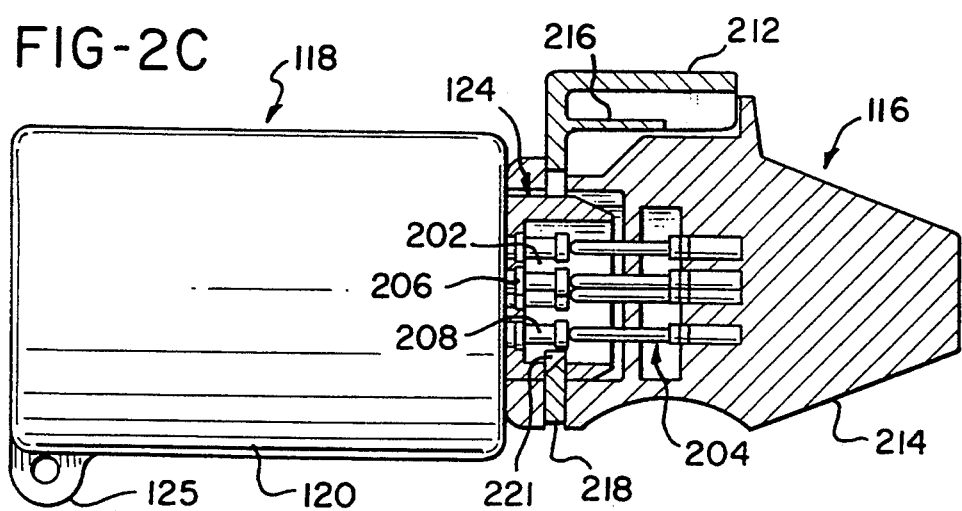

The completed coupling of the adaptor 118 and cable connector 116 is shown in FIG. 2C. The plunger contacts 202 are now abutting their respective contact pins 204. The center shafts 208 of the plunger contacts 202 being recessed in response to the force of the contact pins 204 and the biasing means forcing the center shafts 208 against the contact pins 204 to maintain an electrical connection. The force 222 has been released from push button 212 causing the resilient member 216 to return to its original planar shape and, concomitantly, returning the push button 212 to its original raised position and forcing the blade 218 into the notch 221 such that the adaptor 118 may not be uncoupled unless the blade 218 is removed from the notch 221.

FIGS. 3A–3D and 4A–4C illustrate an adaptor 118 and an ECG cable 110, respectively, constructed in accordance with the present invention. As indicated above, the primary advantage of the invention is the utilization of only one type of ECG cable 110 for any number of different ECG monitors having an adaptor 118 affixed thereto. It should be understood that the particular configuration of the circuit means of the adaptor 118 will depend upon the particular ECG monitor 102 being used. In each case, however, the design of the cable coupling means 124 will be the same. As a result, the same ECG cable may be properly connected to the adaptor 118 irrespective of the type of ECG monitor 102 which is to be used.

Figure 3D:
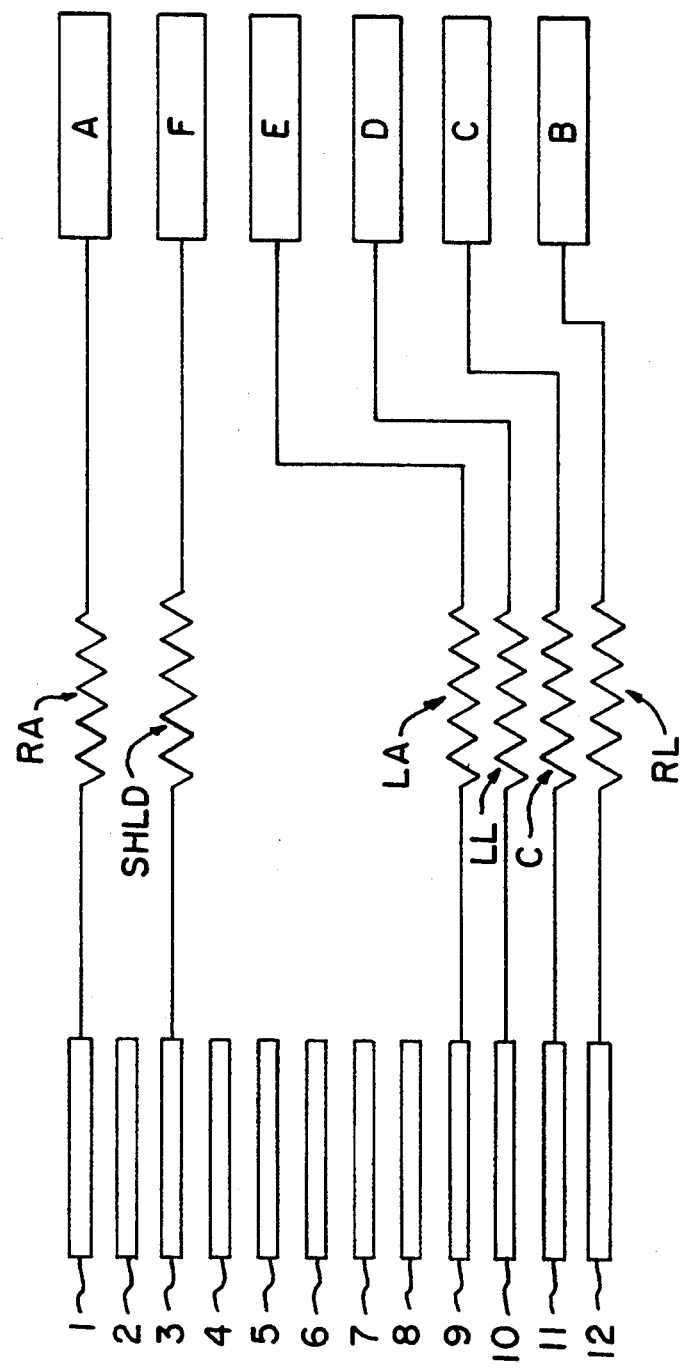
FIG. 3D is a schematic diagram of the circuitry in the adaptor.

In FIG. 3A the machine coupling means 122 having an exemplary pin configuration, such as is adapted to be connected to an ECG monitor sold by Hewlett-Packard Corporation, as the Merlin Model, is shown. Twelve circular elements, or pins, 1 through 12 are inserted into corresponding female receptacles 108 in the input connector 106 of the particular ECG monitor 102. As shown in the circuit diagram of FIG. 3D, circuit means 136 actually includes five signal resistors RA, RL, C, LL, and LA and one shield resistor SHLD. As is well known in the art, RA and LA typically indicate electrical signals obtained from the patient's right and left shoulder area, respectively, and RL and LL generally designate electrical signals obtained from the respective right and left leg area of the patient. An electrical signal from the central area of the chest of the patient flows through resistor C. Those skilled in the art will readily comprehend that other wiring schemes may be used for different ECG apparatuses.

FIG. 3C shows the contact plunger configuration of the cable coupling means 124 of the adaptor 118. Five contact plungers A through E receive electrical signals representative of the heart activity of a patient from the ECG cable 110. Contact plunger F provides a conventional shield connection.

An exemplary wiring diagram for the adaptor 118 is shown in FIG. 3D. As is readily apparent, only inputs 1, 3, and 9 through 12 are required for the Merlin Model ECG monitor. As is known by one skilled in the art, different ECG monitors require different circuits in the adaptor 118. For instance, the Model MD4 ECG Monitor, manufactured by Datascope Corporation, requires only three input electrical signals: the right shoulder RA, left shoulder LA and left leg LL. Those skilled in the art can readily configure the circuit means for any specific ECG monitor.

The ECG cable 110 is shown in detail in FIGS. 4A through 4C. The cable connector 116 has five pins A' through F' configured to contact the corresponding contact plungers A through F of coupling means 124. Electrode block 112 is designed for connection to a maximum of five shielded or unshielded lead wires. The design of a female receptacle adapted to be connected to shielded or unshielded lead wires is well known in the art and, thus will not be further described herein. This ECG cable 110 may be advantageously used, in conjunction with an appropriate adaptor, with any ECG monitor requiring a maximum of five electrical signals to monitor the heart activity of the patient.

The female receptacles 10 through 50 are shown in FIG. 4C. Table 4 provides in tabular form the connections between the individual contact pins 204 of the cable connector 116 and the female receptacles 10 through 50. For instance, receptacle 10 receives electrical signals from the lead wire attached to the medical electrode monitoring the right shoulder area RA of the patient and the signals are transmitted through the ECG cable 110 to contact pin A' of cable connector 116. Similarly, receptacle 20 receives electrical signals from the medical electrode monitoring the right leg area RL of the patient and the signals are transmitted to contact pin E'.

Visual indicia may be superposed on the body of the electrode block 112 indicating which lead wires should be connected to a particular female receptacle. Thus, the ECG cable 110, in conjunction with the appropriate adaptor, may be used with any ECG apparatus requiring a maximum of five electrical signals to monitor the heart activity of a patient. This flexibility allows hospitals, or other medical facilities, to greatly reduce its inventory of different ECG cables.

In another embodiment of the invention, a hospital electrocardiograph patient monitoring system is provided which includes a plurality of electrocardiograph (ECG) monitors and a plurality of adapters therefor. Numerous ECG monitors are available having various ones of a plurality of input connector configurations. Currently, there are approximately twenty-two different input connector configurations in common use on ECG monitors marketed in the United States.

Each adaptor of the hospital electrocardiograph patient monitoring system, which is connected to an associated one of the plurality of monitors, has an appropriate machine coupling means for connection to the associated input connector and an identical cable coupling means. By having identical cable coupling means on each adaptor, identical ECG cables may be connected thereto.

Having thus described the electrocardiograph system of the present invention in detail and by reference to preferred embodiments thereof, it will be apparent that modifications and variations are possible without departing from the scope of the invention defined in the appended claims.

What is claimed is:

1. An adaptor for interconnecting an electrocardiograph apparatus and an electrocardiograph cable including a cable connector connected at one end thereof, said adaptor comprising:

machine coupling means for electrically interconnecting with the electrocardiograph apparatus;

circuit means, electrically connected to said machine coupling means, for conditioning electrical signals so that said electrical signals may be properly received by the electrocardiograph apparatus;

cable coupling means, electrically connected to said circuit means, for electrically interconnecting the cable connector and said circuit means whereby the electrocardiograph apparatus properly receives said electrical signals from the electrocardiograph cable; and attachment means for mechanically securing said adaptor to the electrocardiograph apparatus.

2. The adaptor as recited in claim 1 wherein said attachment means is a lanyard.

3. The adaptor as recited in claim 1 wherein said machine coupling means includes at least one male circular element for electrically connecting with the electrocardiograph apparatus.

4. An adaptor for interconnecting an electrocardiograph monitor and an electrocardiograph cable, said adaptor comprising a housing having machine coupling means mounted on a first end for connecting with the electrocardiograph monitor and a cable coupling means mounted on a second end for properly connecting with the electrocardiograph cable, said cable coupling means including at least one plunger contact comprising a slidable center shaft and biasing means for forcing said center shaft against the cable connector so as to electrically connect with the cable connector.

5. The adaptor as recited in claim 4 wherein said machine coupling means comprises at least one male circular element for electrically connecting with the electrocardiograph apparatus.

6. An adaptor for interconnecting an electrocardiograph apparatus and an electrocardiograph cable, said adaptor comprising:

machine coupling means for electrically interconnecting with the electrocardiograph apparatus;

circuit means, electrically connected to said machine coupling means, for conditioning electrical signals so that said electrical signals may be properly received by the electrocardiograph apparatus; and cable coupling means, electrically connected to said circuit means, for electrically interconnecting the cable connector and said circuit means whereby the electrocardiograph apparatus properly receives said electrical signals, said cable coupling means including at least one plunger contact for electrically connecting with the cable connector, said at least one plunger contact comprising a slidable center shaft and biasing means for forcing said center shaft against the cable connector so as to electrically connect with the cable connector.

* * * * *